United States Patent [19]

Schenck et al.

[11] 3,958,364
[45] May 25, 1976

[54] PRODUCTION OF ALGAL BIO-POLYMERS

[75] Inventors: Paula Schenck, Boston; Patricia L. Foster, Cambridge; William W. Walker, Jr., Allston; Samuel Fogel, Newton, all of Mass.

[73] Assignee: American Bioculture, Inc., Plumsteadville, Pa.

[22] Filed: May 5, 1975

[21] Appl. No.: 574,744

Related U.S. Application Data

[63] Continuation of Ser. No. 421,527, Dec. 4, 1973, abandoned.

[52] U.S. Cl. .......................... 47/1.4; 47/DIG. 10; 210/11
[51] Int. Cl.$^2$ .................. A01G 7/00; C02C 1/00
[58] Field of Search .............. 47/1.4, 58, DIG. 10; 210/54, 11, 2, 15

[56] References Cited
UNITED STATES PATENTS

| | | | |
|---|---|---|---|
| 2,732,661 | 1/1956 | Spoehr et al. | 47/58 |
| 2,908,113 | 10/1959 | Martin | 47/58 |
| 3,197,309 | 7/1965 | Chapman et al. | 47/1.4 |
| 3,546,812 | 12/1970 | Kobayashi et al. | 47/1.4 |
| 3,732,089 | 5/1973 | Megronigle | 47/1.4 X |
| 3,820,281 | 6/1974 | Bigler et al. | 47/1.4 X |
| 3,879,890 | 4/1975 | Chen et al. | 47/1.4 |
| 3,889,418 | 6/1975 | Porter et al. | 47/58 |

*Primary Examiner*—Robert E. Bagwill
*Attorney, Agent, or Firm*—Synnestvedt & Lechner

[57] ABSTRACT

Cultivation of algae to produce long chain polymers having flocculating properties is disclosed. Algae are cultivated in an aqueous nutrient medium until relatively high culture densities are achieved and thereafter under conditions in which the cells become deficient in nitrogen thereby causing the cells to shift from a growth phase in which protein production predominates to a growth phase in which extracellular polymer production predominates. An adequate supply of other nutrients as well as $CO_2$ and light are maintained in the culture medium during the latter phase to insure that a change in cell metabolism is produced by a deficiency in nitrogen. The algae then produce high molecular weight polymers exhibiting strong flocculating activity.

14 Claims, 10 Drawing Figures

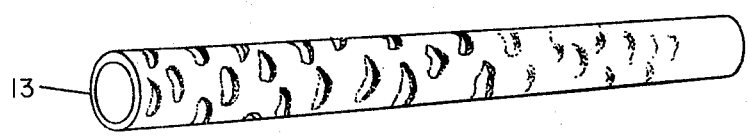
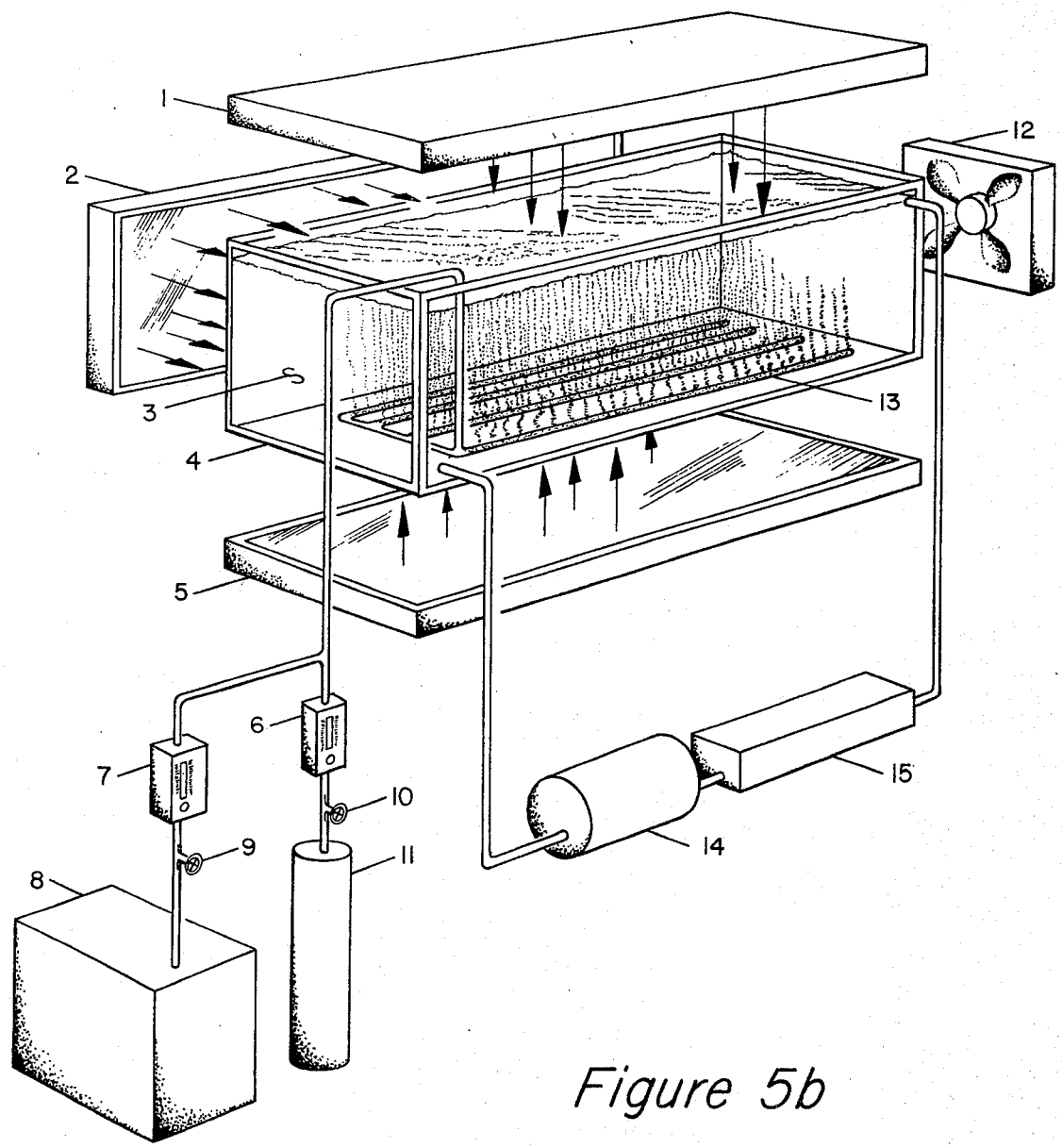
Figure 5a
Figure 5b

PRODUCTION OF ALGAL BIO-POLYMERS

This is a continuation of application Ser. No. 421,527, filed Dec. 4, 1973, now abandoned.

FIELD OF THE INVENTION

This invention relates to the production and use of algae as a source of polymeric materials displaying strong flocculating activity. An important feature of the invention involves the discovery that the growth of algae can be regulated so as to favor the production of large amounts of flocculants, useful in waste water treatment operations for the breakdown and removal of solids, reduction of BOD, and the breakdown of grease blankets. The flocculants are also useful as soil conditioners improving soil tilth, improving aeration, drainage, moisture retention, root development and have utility for other applications where flocculating agents are commonly employed, such as in drilling fluid technology as drilling mud extenders. As is known in the art, products exhibiting flocculant activity in higher concentrations are also useful as surfactants, detergents, emulsifiers and dispersants and products formed in accordance with the invention are of utility for such purposes in appropriate concentrations.

BACKGROUND OF THE INVENTION AND PRIOR ART

The production of algae, as a protein rich food source for animals and humans, as well as a source of other valuable products such as dyes, vitamins and the like, is extensively reported in the Carnegie Institution of Washington publication No. 600, ALGAL CULTURE FROM LABORATORY TO PILOT PLANT, Edited by John S. Burlew and published at Washington, D. C. in 1964. This publication contains studies of the various factors involved in obtaining high yields from cultures of algae, focusing primarily on the species *Chlorella pyrenoidosa* but of applicability to other species of algae as well. In addition, the above publication and other prior art including U.S. Pat. No. 2,732,661 disclose the cultivation of algae under conditions which cause a predominance of intracellular protein, lipid or carbohydrate by regulating the amount of available nitrogen. Production of algae as a source of proteins and lipids, and other materials derived from the algae, are discussed in the Carnegie publication.

According to another body of prior art, utilization of bacterial polysaccharides as flocculating agents, especially for aggregating soil particles, thereby improving soil structure is known. Patents such as U.S. Pat. Nos. 2,780,888 and 2,901,864 teach the application of these bacterially produced biopolymers to the soil as a means for promoting soil aggregation, thereby producing a granular structure which is sufficiently porous to allow air, water, and plant roots to penetrate through the soil. According to these patents, sucrose as a raw material is converted to dextran by innoculating a nutrient medium containing sucrose with a dextran synthesizing bacteria such as *Leuconostoc mesenteroides*. The dextran may be used in granular form or in solution in an aqueous medium and applied to soil.

In addition to the foregoing, long chain synthetic polymers useful as soil conditioning agents which are capable of aggregating soils and useful for other applications where flocculating activity is required, are disclosed in the art. Examples of synthetic polymeric materials useful for increasing aggregation in surface soil are disclosed in Hedrick et al U.S. Pat. No. 2,651,885. According to the Hedrick et al patent, water soluble polymeric electrolytes having a molecular weight of at least 10,000, including polymers of acrylic acid, copolymers of maleic anhydride and the like are provided. These polymeric materials are effective in improving soil structure, but their use has been somewhat limited in view of their high cost.

SUMMARY AND OBJECTS OF THE INVENTION

With the foregoing in view, it is an object of the present invention to provide a new and improved method for producing flocculating agents by the cultivation of algae.

Another important object of the invention is the provision of an economical method of producing flocculating agents, requiring as raw material algae, light, a source of assimilatable carbon and common plant nutrients.

Still another important object of the invention is the production of flocculating agents utilizing readily available and often commonly occurring species of algae.

A more specific object of the invention is the production of flocculating agents from algae by controlling the available nutrients, particularly nitrogen and phosphorus.

Other objects and advantages of the invention will become more apparent from the detailed description of the invention.

Basically considered, the invention involves the discovery that algae can be made to favor the production of flocculating agents by limiting the cellular nitrogen. More specifically, it has been discovered that when an algal culture has used up its available nitrogen supply so that the cells are deficient in nitrogen, and when other nutrients in the medium are available in sufficient quantity that they are not limiting growth factors, the cells will favor the production of high molecular weight extracellular polymers exhibiting strong flocculating activity.

Although the algal produced polymers have not been fully identified, these polymers are ethanol precipitable, anthrone sugar reacting materials and hence are apparently polysaccharides. Filtration through calibrated membranes indicates that these agents having a molecular weight of approximately 100,000. In tests, flocculant activity is not destroyed by proteolytic enzymes, indicating that the polymers are not protein in nature. The flocculants produced according to the invention are primarily extracellular metabolites although with certain species flocculating activity is to some degree also associated with the substance of the algal cells. From a functional point of view, the flocculating agents produced by the invention resemble the bacterial polysaccharides and synthetic polymeric flocculating agents mentioned above.

Conditions for optimizing yields of algae in terms of multiplication of cells, are now well known in the art as reported for example, in ALGAL CULTURE FROM LABORATORY TO PILOT PLANT, referred to above. Basically considered, the algae require a sufficient carbon source usually in the form of carbon dioxide, light as an energy source, a source of nutrients and favorable temperature conditions. The nutrient medium does not differ materially from that used by higher plants, consisting of an aqueous solution of fixed nitrogen, other mineral nutrients and micro-nutrients. The algae are grown in natural sunlight or artificial light which may be supplied for example, by means of lamps sold by the Sylvania Corporation under the trademark Gro-lux lamps.

When algae are cultured in a suitable nutrient medium with adequate light at favorable temperatures as explained in the above-identified publication, there will be an exponential phase of growth in which there is a geometric increase in the number of cells. As the culture continues to grow it reaches a point where the rate of progression slacks off and it thereafter enters a stationary phase in which there is little or no increase in population density, due mainly to the depletion of one or more of the nutrients in the nutrient solution, the inability of light to penetrate the culture, or the lack of carbon dioxide. In the production of flocculants, the invention first involves the culturing of algae under conditions favoring healthy growth so as to maximize yield. When a predetermined cell density is reached as measured by the number of cells or weight of cellular matter per unit volume of medium, culturing is continued under conditions to be described herein so as to favor production of flocculants. According to one form of the invention, the culture is harvested from the initial or nurse tank when it approaches its maximum density, that is, at or near the end of the logarithmic or characterized by maximum yield stage of growth. Typically, densities of from $1 \times 10^7$ to about $1 \times 10^8$ cells per ml, which correspond to between about 0.200 to 2 grams of cellular matter per liter, are achieved before exponential growth ceases and these densities are suitable from the standpoint of the production of flocculants on a commerical scale. The culture is then transferred to a tank where culturing is continued under conditions favoring flocculant production. During this phase of growth, culturing is carried out under conditions of nitrogen deficiency. During exponential growth, when other growth factors are non-limiting, cellular nitrogen is about 10% dry weight. In contrast, flocculant production in large quantities is observed when cellular nitrogen is below about 5% dry weight.

The invention is particularly applicable to the culturing of green and non-nitrogen fixing blue-green algae. Excellent results are obtained using certain green, unicellular algae which are normal inhabitants of soil and fresh water. A preferred genus is *Chlamydomonas*. Within this genus, cultures of the species *Chlamydomonas mexicana* have been found to yield exceptional results. A further example of an alga to which the techniques of the invention apply is *Chlorella*, of which *Chlorella pyrenoidosa* is exemplary.

When cultured according to the invention, *Chlamydomonas mexicana* has been found to produce an active flocculating agent constituting 80% of the total culture dry weight. The agent is stable under normal environmental conditions; no loss in flocculant activity has been detected in cultures stored at room temperatures for up to 6 weeks.

In carrying out the invention it is important that the cultures be exposed to adequate light and be provided with an ample supply of carbon dioxide during the flocculant producing phase as well as the growth phase. During the flocculant producing phase, it is preferred that the cultures be exposed to light substantially continuously. Under conditions of continuous light exposure, larger yields of flocculating agent are produced. It is theorized that this is because the algae draw on their carbohydrate reserve when light is not available to them thus consuming or restricting the production of flocculating agent.

In the description which follows, reference is made to the accompanying drawings in which:

FIG. 5a illustrates one part of the apparatus shown in FIG. 5;

FIG. 5b illustrates apparatus suitable for the production of cultures according to the invention;

Figure 1:
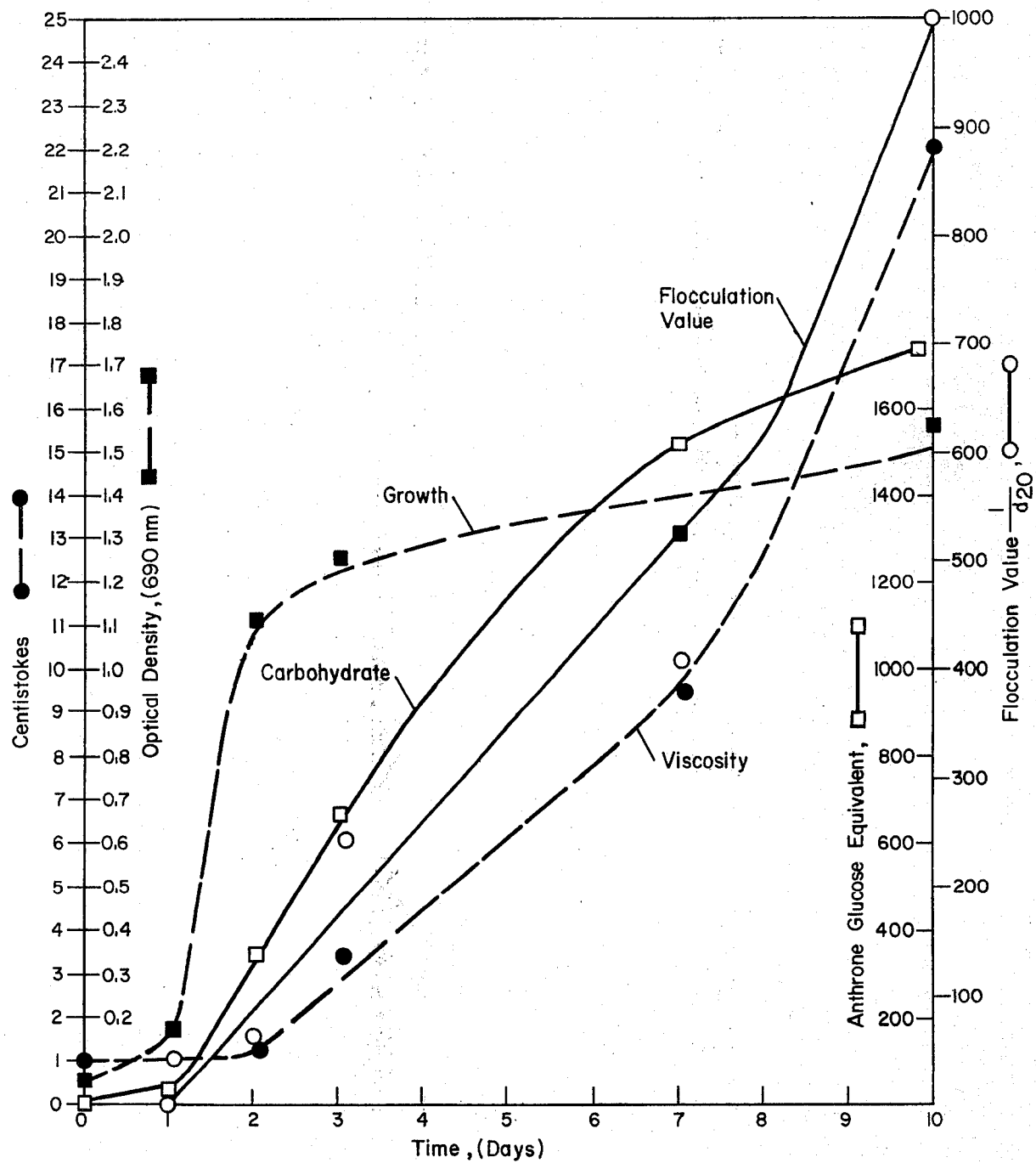
FIG. 1 is a plot of culture growth, carbohydrate, viscosity and flocculation value as a function of time.

The examples which follow will serve as illustrative of the various aspects of the invention using the green alga species *Chlamydomonas mexicana* and *Chlorella pyrenoidosa*. In certain examples set out below the nutrient medium of Table 1 was employed for growth and flocculant production phases of culturing algae of the species *Chlamydomonas mexicana*.

TABLE I

| | |
|---|---|
| $KNO_3$ | .180 g/L |
| $MgSO_4.7H_2O$ | .050 g/L |
| $CaCl_2.2H_2O$ | .166 g/L |
| $KH_2PO_4$ | .050 g/L |
| Trace Elements | .12 ml/L |
| Iron EDTA | .12 ml/L |
| Trace Elements | Iron EDTA |

| | | | |
|---|---|---|---|
| $H_3BO_3$ | 2.86 g/L | Disodium EDTA | 26.1 g/L |
| $MnSO_4.H_2O$ | 1.23 g/L | $FeSO_4.7H_2O$ | 24.9 g/L |
| $ZnSO_4.7H_2O$ | .22 g/L | NaOH (1N) | 263 ml/L |
| $MoO_3(85\%)$ | .017 g/L | Water to | 1 L |
| $CuSO_4.5H_2O$ | .079 g/L | | |
| $CoCl_2.6H_2O$ | .041 g/L | | |

Various nitrogen compounds, as for example, ammonium nitrate, ammonium chloride or urea may be used in place of potassium nitrate. When ammonium chloride is used, pH must be continuously adjusted to neutrality to avoid excess culture acidity. As indicated below, in certain of the examples the amount of nitrogen was varied from that given above. In other examples, culturing was continued in the nutrient medium until the nitrogen in the medium was used up.

The term polysaccharide is used herein to mean a material which is an ethanol precipitable, non-dialyzable, anthrone sugar reacting material. In the examples, viscosity is measured by a calibrated Cannon-Penske viscometer and results are expressed in centistokes. Whole culture viscosity is approximately equal to the viscosity of centrifuged cell-free supernatent. Culture growth is measured by a Bausch & Lomb spectronic 20 colorimeter at a wave length of 690 nm. Cell number and culture dry weight are linear functions of optical density up to an optical density of 1. Dry weight is also measured directly or estimated from the relationship $g/l$ = O.D. 690/2 which has been empirically derived, wherein $g$ is grams of cell-matter, L is volume of algae and medium in liters and optical density (O.D.) is measured at 690 nanometers.

When cells from an exponentially growing culture of *Chlamydomonas mexicana* are isolated by centrifugation, their carbohydrate content is around 35% of cellular dry weight. Because of the fragility of these cells and the tendency for capsular materials to slough off, it is difficult strictly to classify the carbohydrates as extracellular. What can be said in general is that when cultures reach the end of exponential growth, about 50% of the total culture carbohydrate is soluble and cell free (isolated by centrifugation). Twenty-four hours later up to 90% of whole culture carbohydrate is soluble and cell free. Approximately 90% of soluble cell free carbohydrate is precipitable by 2 volumes of ethanol. Unless otherwise stated all carbohydrate determinations are whole culture determinations.

Cellular nitrogen content is determined by the Kjeldahl nitrogen method (Standard Methods, 13th Edition, 1971) in vegetative or early zygote cultures. In older cultures cellular nitrogen is computed based on the culture dry weight and initial nitrate nitrogen level. Nitrate nitrogen is also determined by Standard Methods (13th Edition, 1971).

Example 1

The green algal species *Chlamydomonas mexicana*, strain No. 729, (Indiana University Culture Collection) was placed aseptically in 250 ml Erlenmyer flasks containing 50 ml of sterile medium prepared as in Table 1 and incubated until the optical density at 690 nm reached 0.5 (250 mg/L dry weight). The entire culture was transferred to a 1 L Erlenmyer flask containing 500 ml of the same medium. This medium provided for continued exponential growth for about one more day at which point cellular nitrogen was at about 5% by weight as will be shown herein below. The culture was bubbled constantly with 5% $CO_2$ in air at a light intensity of 500 boat candles. Lighting was continuous for the duration of the experiment. The results of culturing as described above over a 10 day period are shown in FIGS. 1-3 and Table II.

FIG. 1 is a plot of culture growth, carbohydrate, viscosity and flocculation value as a function of time. Flocculation value in this example is a measure of the minimum amount of active material required to produce the first visible aggregation of clay particles and provides a rating of active materials by comparing the lowest dosage required to produce visible aggregation. A suspension of kaolin clay is prepared with an average particle diameter of non-flocculating kaolin clay being 3.2 microns. The average particle diameter of kaolin at the smallest dosage which causes visible aggregation is 20 microns. The inverse of the volume required to cause a particle diameter of 20 microns, is referred to as $1/d_{20}$ and is used as a measure of flocculation value. An initial substrate nitrogen level of 25 mg/l was chosen after taking into account such growth regulating factors as light intensity, $CO_2$ and temperature. This level of substrate nitrogen resulted in the production of 250 mg of algal dry weight having a nitrogen content of 10%. This dry weight corresponds to an optical density (690 nm) of 0.5 which occurred during the early exponential growth phase. As can be seen in Table II, FIGS. 1 and 3 culturing was continued for about 10 days.

TABLE II

| Day | Growth OD (690 nm) | Cells/ml | Cellular Dry Weight g/L | %N |
|---|---|---|---|---|
| 0 | .045 | $1 \times 10^6$ | .022 | 10 |
| 1 | .168 | $2.5 \times 10^6$ | .0840 | 10 |
| 2 | 1.08 | $1.9 \times 10^7$ | .540 | 4.6 |
| 3 | 1.25 | $2.5 \times 10^7$ | .620 | 4.0 |
| 7 | 1.29 | $2.6 \times 10^7$ | .640 | 3.9 |
| 10 | 1.58 | $3.1 \times 10^7$ | .790 | 3.2 |

All measurements are based on whole culture determinations except for cellular dry weight which is obtained from centrifuged exponential cells. Cellular dry weight from cultures in the post exponential phase is estimated from the optical density according to the empirical relationship mentioned above.

The data presented in FIG. 1 and Table II shows that culture carbohydrate, flocculation value and viscosity do not parallel culture growth but increase after growth ceases. By the end of exponential growth (OD 690 = 1.0) cellular nitrogen has fallen to 5% of culture dry weight. This post exponential phase (starting with day 2 in the illustrative example) is the flocculant production phase.

Figure 2:
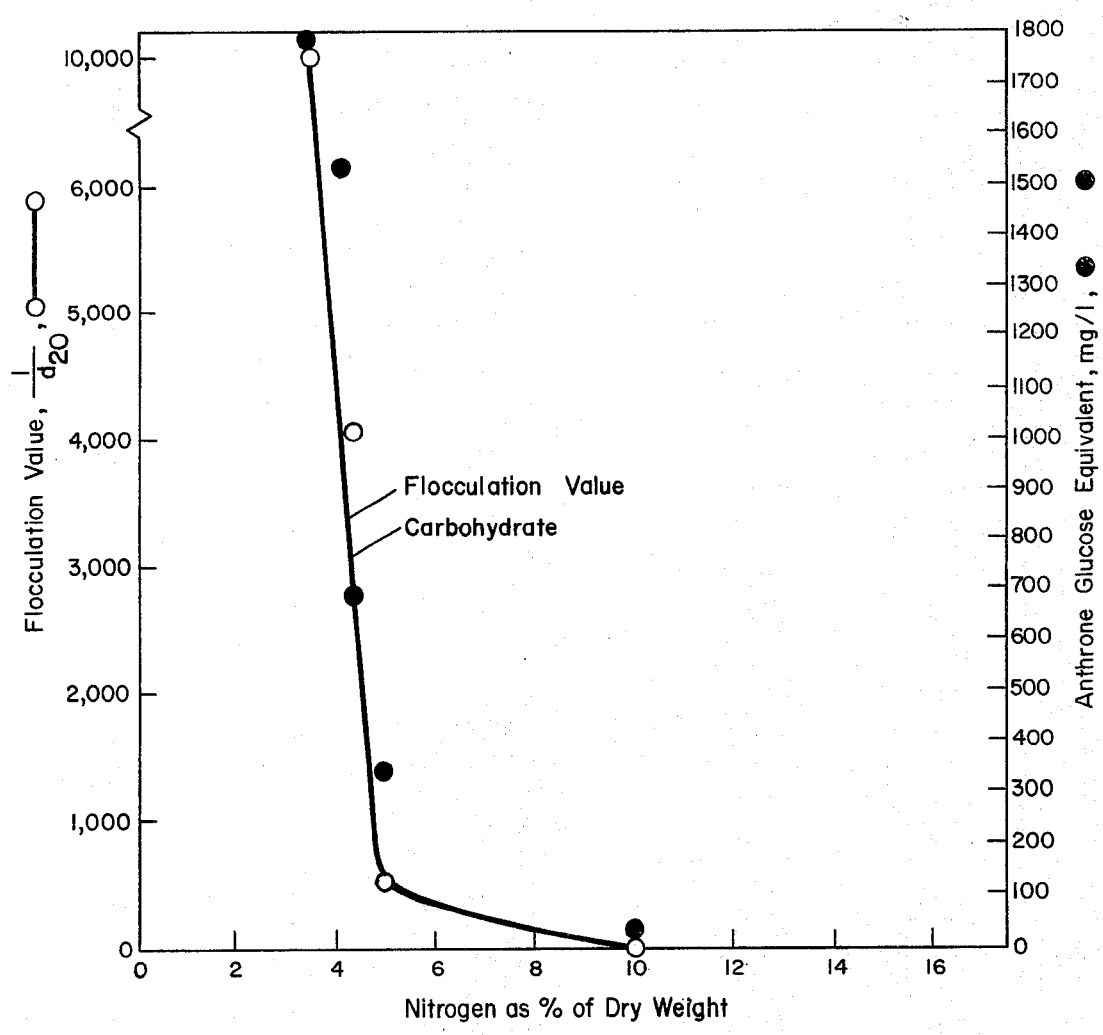
FIG. 2 illustrates the relationship between flocculation value and cellular nitrogen.

The relationship between flocculation value, carbohydrate contents and cellular nitrogen is illustrated in FIG. 2. As can be seen in FIG. 2, substantially no flocculant is produced until cellular nitrogen reaches about 5% of dry weight. The flocculant value and carbohydrate content are seen to rise in an exponential fashion as the cellular nitrogen content falls below 5%.

Figure 3:
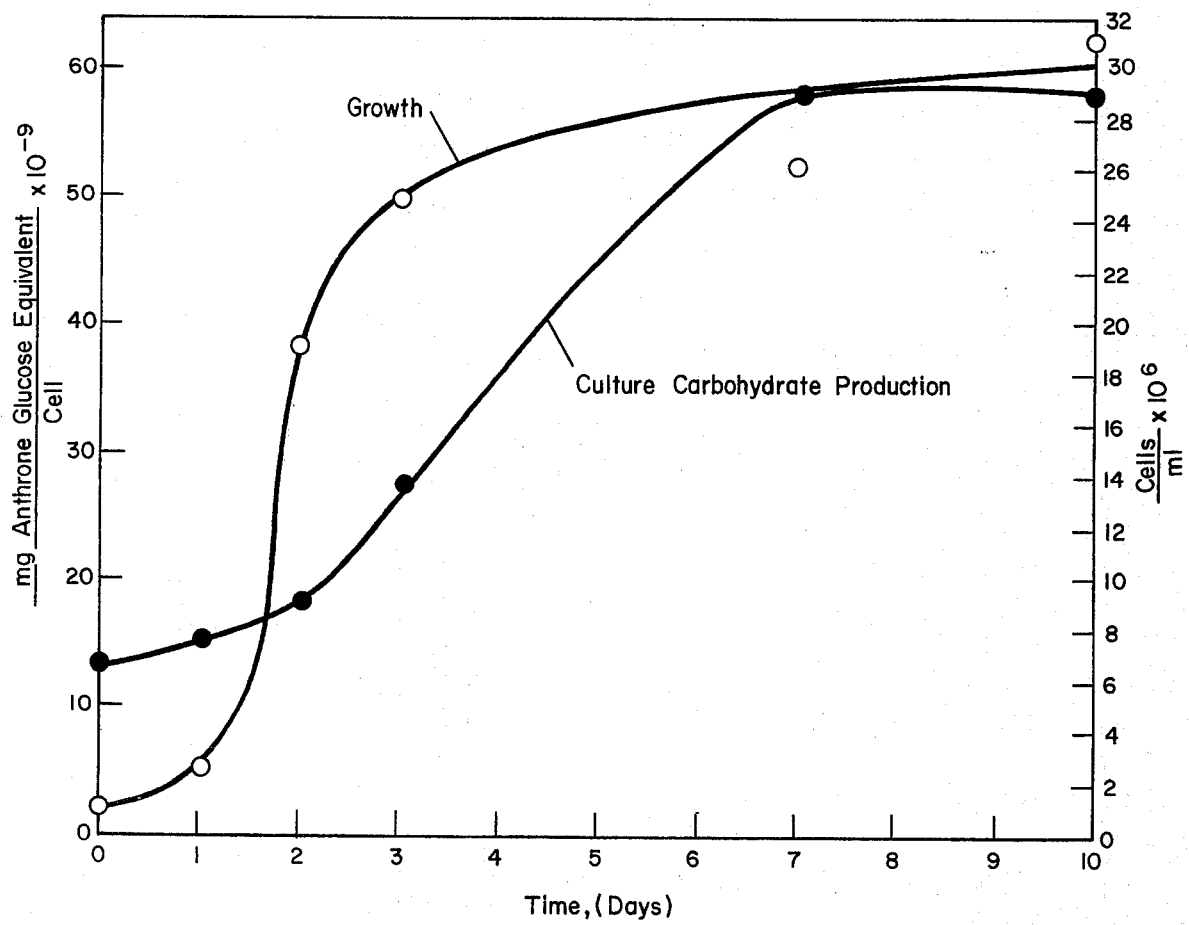
FIG. 3 is a plot of carbohydrate/cell and cell productions versus time.

FIG. 3 shows plots of carbohydrate per cell versus time. It is apparent that the amount of carbohydrate (i.e., flocculant) per cell begins to increase as cell multiplication slows (day 2) and reaches a maximum 5 days later. Thus, the phase of rapid cellular multiplication is clearly separated from the phase of maximum cellular polysaccharide production. The slope of the flocculant production curve represents the rate of flocculant production. During rapid cell multiplication this rate is less than 1/3 the rate found during stationary phase of growth.

Example II

Figure 4:
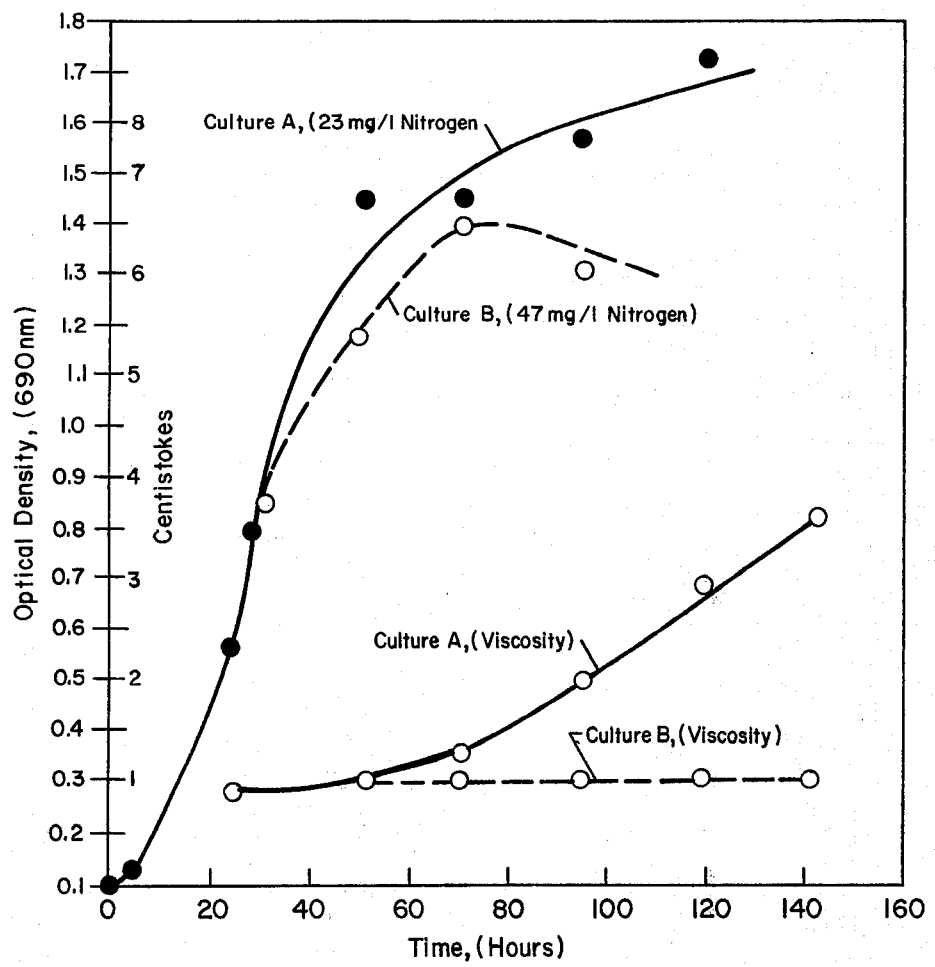
FIG. 4 shows plots of culture growth as measured by optical density and viscosity for cultures grown on medium of different nitrogen concentrations.

For comparison purposes, two 8 inch diameter plexiglass cylinders containing 34 liters of nutrient medium were inoculated with *Chlamydomonas mexicana* from intermediate flasks to produce a starting O.D of 0.1 at 690 nm (50 mg/L). Five percent of $CO_2$ in air was bubbled through air stones positioned on the bottom of the cylinders. Culture A contained about 23 mg/L nitrate nitrogen and Culture B, about 47 mg/L of nitrate nitrogen. The nitrient medium composition was otherwise identical to the medium of Table I. The nitrogen in the nutrient medium composition of Culture B was two times more concentrated than Culture A. Culture growth as measured by optical density and viscosity are shown in FIG. 4. Culture A showed the characteristic phase of exponential growth followed by the phase of flocculant production as indicated by the increase in viscosity. Culture B, however, showed only the phase of exponential growth. Culture A, reached a cellular nitrogen content of 5% of dry weight by 50 hours whereas Culture B remained at 10% cellular nitrogen for over 100 hours.

Example III

This example illustrates use of one form of culturing system well suited for carrying out the invention and shows how the manipulation of culture nitrogen levels can be used to produce algal flocculants in a large scale semi-continuous culturing process. The flocculant produced from such a system lends itself for direct use although it may be further concentrated if desired.

The culture vessels employed, one of which is shown at 4 in FIG. 5b consisted of two rectangular glass tanks having a capacity of 160 L each. The culture tanks 4 were continuously illuminated with fluorescent light on all four sides from lamps 1, 2 and 5 and a fourth lamp, which is not shown for clarity of illustration. The culture medium was continuously bubbled with 5% $CO_2$ from cylinder 11, via valve 10 and flowmeter 6. Air is provided by means of compressor 8, valve 9 and flowmeter 7. Both air and $CO_2$ enter the tank through air stones 13, one of which is also shown in FIG. 5a. Temperature was maintained at 25° C by use of a circulation system including pump 14, heat exchanger 15 and a fan 12. The first culture tank I is operated as the vegetative growth chamber whereas the second tank II is operated as the flocculant production chamber. At initial start-up, the first tank is inoculated with culture (Chlamydomonas mexicana) in 80 liters of the aqueous medium of Table I which contains 25 mg/L N. This level of nitrogen results in an algae density of 250 mg/L of 10% nitrogen by weight vegetative cells (O.D. 690 = 0.5). When the first tank reaches this density, a portion of its contents, preferably about one-half of its volume, is transferred to the second tank. Tank I then receives nutrient medium (25 mg/L N) to original volume. Tank II receives an equal volume of water. Both tanks are permitted to grow to a final optical density of about 0.5, which corresponds to cells having a nitrogen content of 10% in Tank I, and less than 5% in Tank II.

Figure 6:
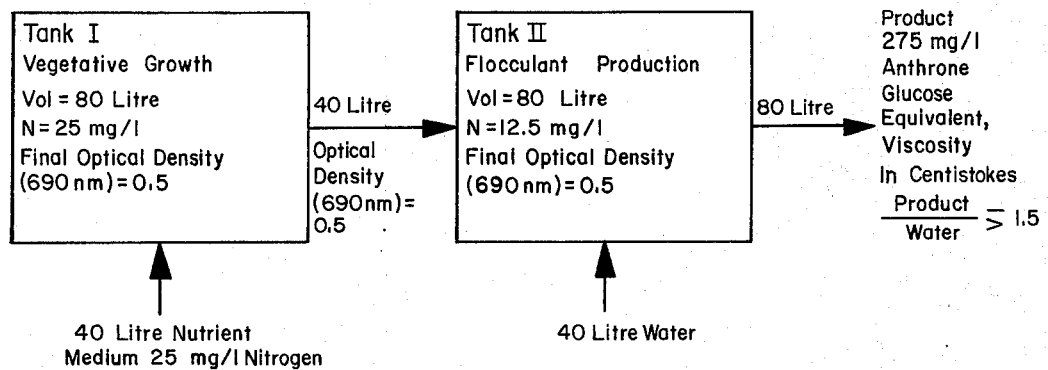
FIG. 6 is a flow chart illustrating a process for the production of flocculants according to the invention.

Flocculant accumulates in Tank II. The contents may be removed and used as is or after the cells are separated as by centrifugation, as desired. The system is schematically depicted by the flow chart of FIG. 6 and is capable of operation as described every 2–3 days.

As intimated from Example I, another mode of carrying out the invention involves culturing under conditions for producing flocculants in the same vessel in which vegetative growth occurs. We have achieved the production of extracellular polymers from Chlamydomonas mexicana out of doors in shallow 12 foot diameter pools provided with $CO_2$ enriched air. It is preferred that the contents of the pools be vigorously mixed to prevent sedimentation of the algae. Viscosities similar to those obtained in Example III can be obtained under proper light and temperature conditions when nutrient levels are controlled as taught herein.

It is important that adequate levels of other nutrients besides nitrogen be maintained in the nutrient solution to support growth. In carrying out the invention, phosphorous levels must be high enough to satisfy exponential growth requirements. If cellular phosphorous levels are too low, then growth may be limited by lack of phosphorus with the result that cellular nitrogen never falls below the level required for appreciable flocculant production. Phosphorus requirements for healthy cell growth are generally understood by those in the art. If uncertainty exists as to a particular species, a few experimental runs will establish adequate phosphorus levels.

The substances in Chlamydomonas mexicana cultures responsible for viscosity, anthrone sugar reaction as well as flocculant activity are ethanol precipitable, non-dialyzable and therefore are considered to be high molecular weight polymers.

Example IV

A mesophilic strain of Chlorella pyrenoidosa (No. 343) was obtained from the University of Indiana algae collection. Cultures were grown in Fernbach flasks under continuous aeration and white light of 400 fc intensity. A nutrient medium of the following composition was employed.

| Compound | g/L | Micronutrients | g/L |
|---|---|---|---|
| $CaCl_2\text{-}H_2O$ | .016 | $H_3BO_3$ | 2.86 |
| $MgSO_4\text{-}7H_2O$ | .250 | $MnCl_2\text{-}4H_2O$ | 1.81 |
| $KNO_3$ | .300 | $ZnSO_4\text{-}H_2O$ | .22 |
| $K_2HPO_4$ | .030 | $MoO_3$ | .017 |
| $NaHCO_3$ | .020 | $CuSO_4\text{-}5H_2O$ | .079 |
| Iron (EDTA) | .005 | $CoCl_2\text{-}6H_2O$ | .041 |
| Micronutrients | 1 ml/L | | |
| Distilled Water | 1 l. | | |

Figure 7:
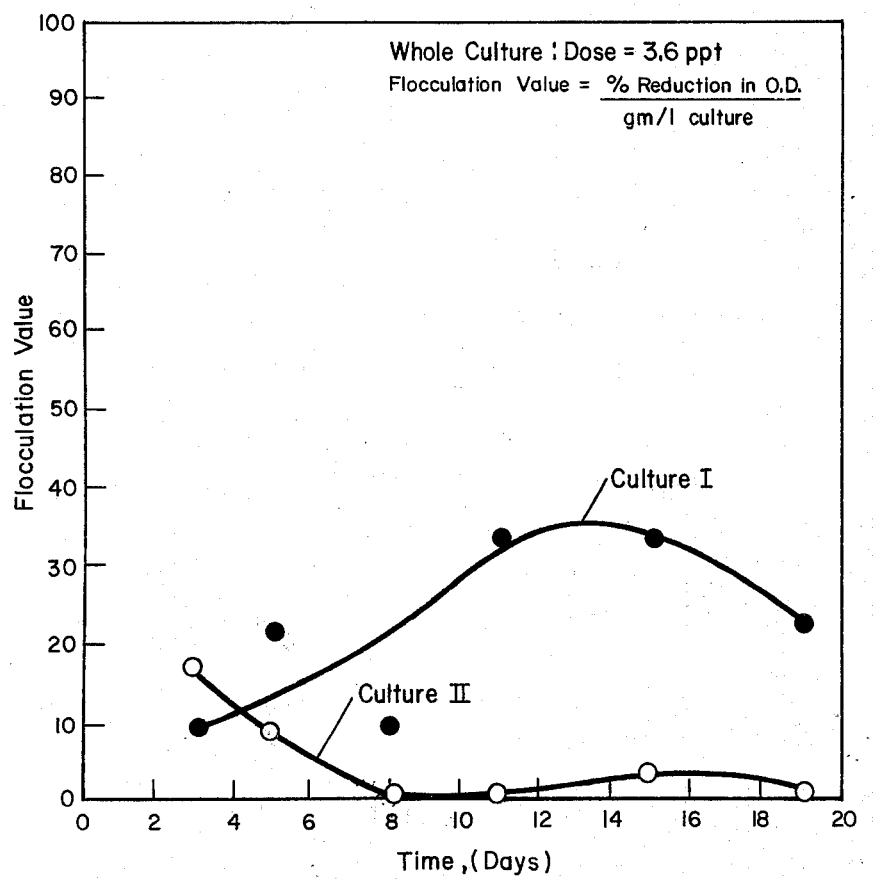
FIG. 7 illustrates flocculant values of cultures of Chlorella of different cellular phosphorous contents.

Flocculant production by Chorella pyrenoidosa was studied under two conditions. Culture I had sufficient cellular nitrogen and phosphorous to produce a cellular nitrogen and phosphorous content of 5.1 and 0.58% respectively by day 11. Culture II contained the same nitrogen level as Culture I but was phosphorous deficient. FIG. 7 shows a plot of flocculation values versus time.

In assaying flocculation, the following procedure was followed. Kaolin clay stock and diluent solutions were prepared as indicated:

| | |
|---|---|
| Kaolin Stock | 0.1 g/l $MgSO_4\text{-}7H_2O$ |
| | 0.1 g/l NaCl |
| | 0.1 $NaHCO_3$ |
| | 0.15 g/l $CaCl_2\text{-}2H_2O$ |
| | 0.2 g/l Kaolin (Fisher) |
| | pH adjusted to 7 with HCl |
| | Stock stirred two days before use |
| Diluent | 0.1 g/l $MgSO_4\text{-}7H_2O$ |
| | 0.1 g/l NaCl |
| | 0.1 g/l $NaHCO_3$ |
| | 0.15 g/l $CaCl_2\text{-}2H_2O$ |
| | pH 8.6 |
| Iron Stock | 1.7 g/l $FeCl_2\text{-}4H_2O$ |

Flocculations were carried out in 12 test beakers containing 28 ml of kaolin suspension each. The suspension was made by adding 240 ml Kaolin Stock and 160 ml diluent. 0.04 ml of Iron Stock was added and the mixture stirred for 30 minutes (the $O.D._{600} = 0.250$, PH = 7.6). Twenty-eight ml of the kaolin mixture was dispensed into 50 ml beakers. Flocculant was added to each beaker with 30 seconds of rapid stirring in 30 second intervals. After addition, beakers were stirred for one hour at 30 rpm. In 30 second intervals, the beakers were gently agitated and 6 ml poured into cuvettes. After 30 minutes of settling, the O.D. (at 600 nanometers) of each cuvette was read at 30 second intervals. One control was run with each 6 test beakers. An $O.D._{600}$ of 0.250 corresponds to a kaolin concentration of 120μg/ml. The 28 ml assay volume therefore contained 3360μg kaolin. Control cuvettes usually had an $O.D._{600} = 0.180$, equivalent to 2420μg kaolin. A 60 percent reduction of relative O.D., therefore, correspond to a flocculation of 1450μg Kaolin.

Although in FIG. 7 both cultures had identical growth kinetics only culture I showed significant flocculant activity. The maximum flocculation value (Culture I) occurred between about day 11 and day 15. At day 11 Culture I and II had a similar cellular nitrogen level (5.1 versus 4.3% respectively), but differed significantly in cellular phosphorous (0.58 versus 0.21% respectively). The unusually low phosphorous level in Culture II has been found to correlate with the absence of flocculant activity. Since Culture II was found to contain two to three times greater dialyzable (small molecular weight) saccharides than Culture I, it is theorized that low cellular phosphorous levels cause depolymerization of polysaccharides or inhibit their formation.

Under certain circumstances, we have observed that phosphorous deficient Chlorella cells can be made to produce flocculants. As is recognized in the art, an actively growing population of Chlorella consists primarily of D or "dark" cells which are characterized by being small but with high photosynthetic and low respiratory activity. When D-cells are transferred to a medium deficient in nitrogen they can undergo a transistion to L cells which in turn can undergo division. These L or "light" cells are somewhat larger than D-cells having low photosynthetic and high respiratory activity. By way of comparison these cells have an average weight of $6 \times 10^{-11}$ gms/cell as compared with the weight of dark cells which averages $2 \times 10^{-11}$ gms/cell. At low phosphorus levels, i.e. below about 0.3% of dry weight, L-cells have been observed sometimes to give rise to flocculant activity. However, we have found that from the standpoint of maximizing productivity, phosphorous levels of about 0.3% dry weight and preferably above about 0.5% dry weight should be maintained.

Example V

In order to illustrate the effectiveness of the flocculants of the invention, as compared with a polystyrene sulfonate flocculating agent, comparative filtration rates through filter cakes were measured by the following procedure, which consists of two separate steps:
1. dispersal of the flocculant into the kaolin suspension;
2. filtration of the liquid through the clay.

A two blade marine type propeller was used to mechanically mix flocculant with the colloidal clay kaolin. Constant mixing speed was obtained by attaching a tachometer to the stirring shaft. Time and speed of mixing was held constant for each dose of flocculant.

Flocculant materials prepared as in Example I or polystyrene sulfonate were added dropwise to a mechanically stirred kaolin suspension at a clay concentration of 1 g/100 ml. The flocculant solutions ranged in concentration from 0.1 g/L (0.01%) to 1 g/L (0.1%). The final volumes of flocculant-clay suspensions were held constant. Measured parameters for the mixing step include:

$M_s$ = speed in RPM of shaft (constant)
$M_t$ = total time in mixing (constant)
$D_P$ = dose of flocculant in ml (independent variable)
$C_P$ = concentration of flocculant solution (constant)
$D_k$ = ml of stock kaolin suspension (constant)
$C_k$ = concentration of stock kaolin suspension in mg/l (constant)
$V_m$ = final volume after mixing (constant)

The filtration apparatus consisted of Buchner funnels 47 mm diameter by 50 mm height with stopcocks in the stem to provide controlled time. Glass filter paper of less than $2\mu$ pore size was used. The collecting Erlenmyer flasks were connected to a manifold pretested to draw equal vacuum from each port. A small vacuum pump and a mercury manometer were used to produce and monitor the vacuum.

The mixed flocculant - kaolin suspension was transferred from the beakers to the funnels which were maintained under a vacuum to seal the filter paper to the funnel bottom. Stopcocks were closed and the suspension allowed to settle. Subsidence and clarity of the supernatent were noted. The suspensions were filtered and then re-filtered. The volume collected upon refiltration with constant vacuum for a constant length of time was measured. A measure of filtration was taken as the ratio of the refiltration rate of the control to the refiltration rate of i.

$$f = \frac{\text{refiltration rate of control}}{\text{refiltration rate } i} = \frac{V_{F_c}/f_t}{V_{F_i}/f_t}$$

$i$ = flocculant-kaolin suspension
Measured parameters were:
$P$ = vacuum in inches H (constant)
*$V_m$ = initial filtration volume (constant)
$f_t$ = refiltration time (constant)
*When $V_m$ exceeded 100 ml the difference was discarded from supernatent.
$V_{F_i}$ = volume collected after refiltration (dependent variable)
$V_{F_c}$ = volume collected after refiltration control (constant)

Figure 8:
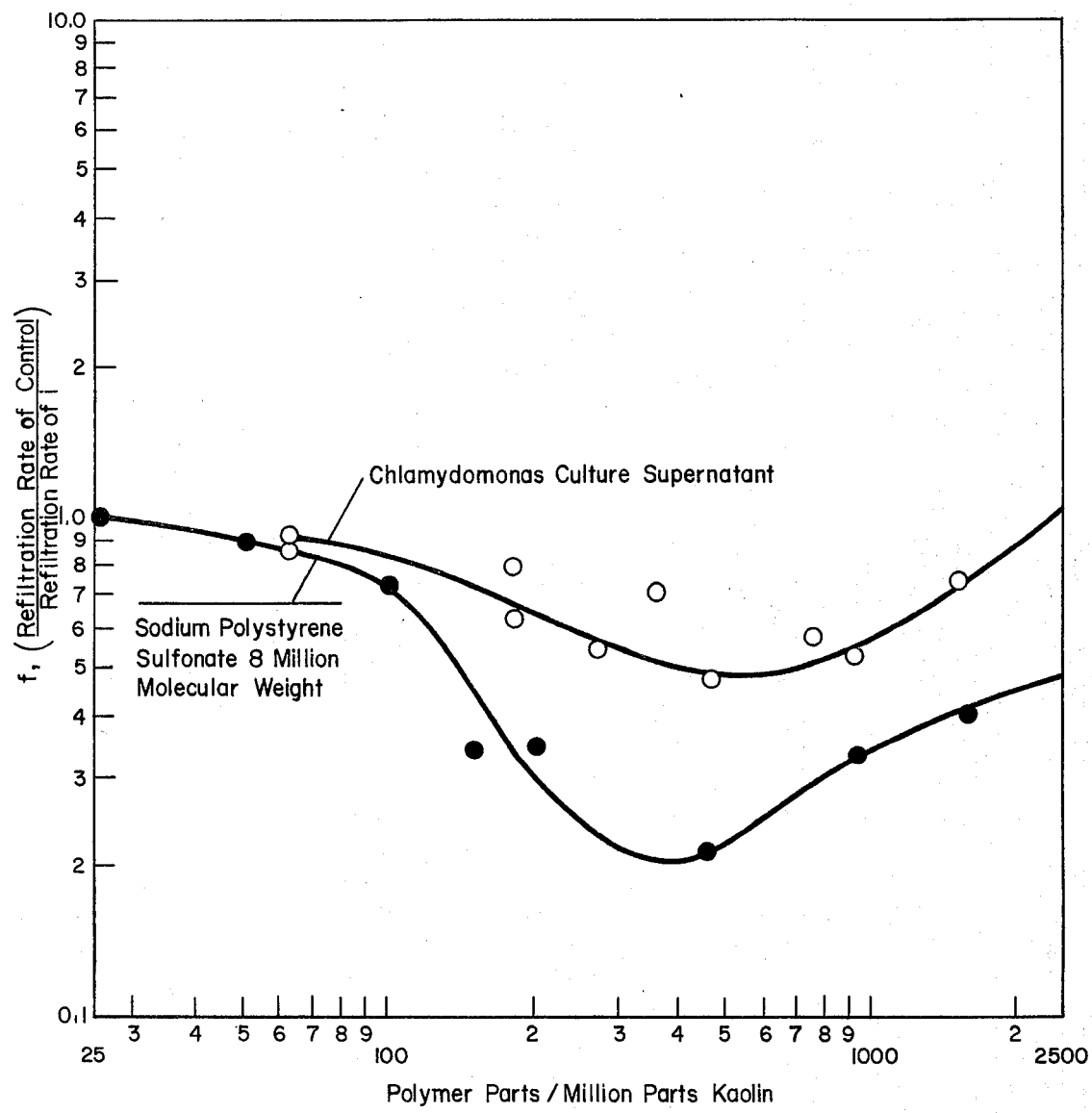
FIG. 8 illustrates flocculation value of cultures formed according to the invention as compared with a polystyrene sulfonate flocculating agent.

FIG. 8 is a plot of filtration rate versus parts polymer to million parts of kaolin. 8 Million molecular weight sodium polystyrene sulfonate and an algal flocculant from *Chlamydomonas mexicana* cultured as described herein were compared. Both polymers or flocculant react with the clay at a polymer to clay ratio of 1 to 5000.

Example VI

As indicated above, algal flocculants are an effective aid in the coagulation of solids in waste water. Specifically, we have found that the use of *Chlamydomonas mexicana* algal flocculant in conjunction with lime results in the production of larger, denser and therefore faster settling flocs than is the case with lime alone. The amount of lime required appears to be less as a result of the use of the algal flocculant. In one example, screened influent from the Deer Island Sewage Treatment Plant in Boston, Massachusetts was flocculated with lime and lime/algae flocculant using the jar test flocculation procedure described in Example IV. The flocculants which were prepared in accordance with Example I, were added in a rapid mix, slow addition fashion and stirred for 1 minute in beakers. The beakers were then placed on a Phipps and Bird Stirrer at 6 rpm for 5 minutes and a final 20 rpm for 30 minutes. At the end of 30 minutes the settling time for subsidence to clear 95% of the supernatent volume was recorded.

Lime was applied as a 10 g/L slurry and in sufficient quantity to reach the desired pH. One ml of *Chlamydomonas mexicana* flocculant was prepared in accordance with the technique of Example III (5 g/L, viscosity = 30 centistokes) and was added to each 1 L of sewage.

The effect of algae flocculant and lime compared to lime alone is seen in Table III. Lime doses necessary to produce pH 10, 10.5 and 11 were compared. The lime and algae flocculant caused the flocculated sewage to settle 10 times faster than lime alone at pH 10. and 10.5. No difference between the two are observed at pH 11 although lime and algal flocculant produced a larger floc size.

TABLE III

| pH | Settling Time Ratios (minutes) (lime/lime & Algal Flocculant) |
|---|---|
| 10.0 | 10/1 |
| 10.5 | 10/1 |
| 11.0 | 1/1 |

Examples VII and VIII

Polymeric substances such as polyacrylamides, bacterial polysaccharides and alginic acid improve soil structure by forming water stable aggregates which in turn improve flow and air penetration into soil. The following examples are illustrative of the soil conditioning properties of Chlamydomonas mexicana on western calcareous soils.

Example VIII illustrates the water stable aggregate formation resulting when Chlamydomonas flocculating agent is mixed with soils at relatively high dosages. Example VII illustrates the effect of a relatively low dose of Chlamydomonas flocculating agent on soils under field conditions.

In carrying out Example VII, a dry calcareous soil (20% clay, 53% silt and 27% sand) was passed through a 1 mm sieve to remove particles greater than 1 mm. Fifty gram portions of sieved soil were mixed with algae cultures having flocculant activity. Culture dry weight to soil dry weight ratios of 1:1000, 1:2500, and 1:5000 were made. A control consisting of algae free culture medium was also mixed with soil. Mixing was carried out for 5 minutes with a spatula. The samples were dried at 50°C to a soil moisture of around 10%. This moist soil was passed through a 2 mm sieve and the artificial aggregates formed greater than 1 mm were used for the aggregate stability study.

Aggregates less than 2 mm and larger than 1 mm in size were dried at room temperature and wet sieved by direct atmospheric immersion for 10 minutes. (Method of Soil Analysis Agronomy Monograph No. 9, Part I, pp. 511–519.) A nest of sieves was used consisting of 1, 0.5, 0.25, 0.1 and 0.05 mm sieves. The dry weight soil retained on top of each sieve was determined. The results are listed below:

TABLE IV

| | Chlamydomonas Flocculant to Soil Ratio (w/w) | % Retained | | |
|---|---|---|---|---|
| | | >.1 mm | >.25 mm | >1 mm |
| (.1% mixture) | 1:1000 | 96 | 74 | 60 |
| (.04% mixture) | 1:2500 | 96 | 84 | 41 |
| (.02% mixture) | 1:5000 | 58 | 24 | 11 |
| | control | 37 | 25 | 13 |

The results show that nearly five times more soil is retained on the 1 mm sieve at a dose of 0.1% of flocculant in soil than is retained by the 1 mm sieve of the control or untreated soil. At the intermediate dose of flocculant to soil of 1:2500, three times more water stable aggregates are retained on the 1 mm sieve when compared to the control. Sixty-four percent more soil is retained on all sieves greater than 0.1 mm in the low flocculant to soil dose compared to the untreated soil.

In Example VIII, triplicate plots of 81 ft$^2$ each were given the following treatment:
 a. control (water)
 b. Chlamydomonas flocculant 12.5 lb/acre
 c. Chlamydomonas flocculant 50 lb/acre
 d. Chlamydomonas flocculant 200 lb/acre Flocculant was prepared as in Example I. Quantities are measured in terms of pounds of dry weight.

Sixty-four gallons of each treatment product was applied per plot. Each plot was then rototilled to a depth of 6 inches after soil moisture reached a tillable level. Soil structure changes were assessed by the following measurements: wet sieving, infiltration and penetration resistance.

Figure 9:
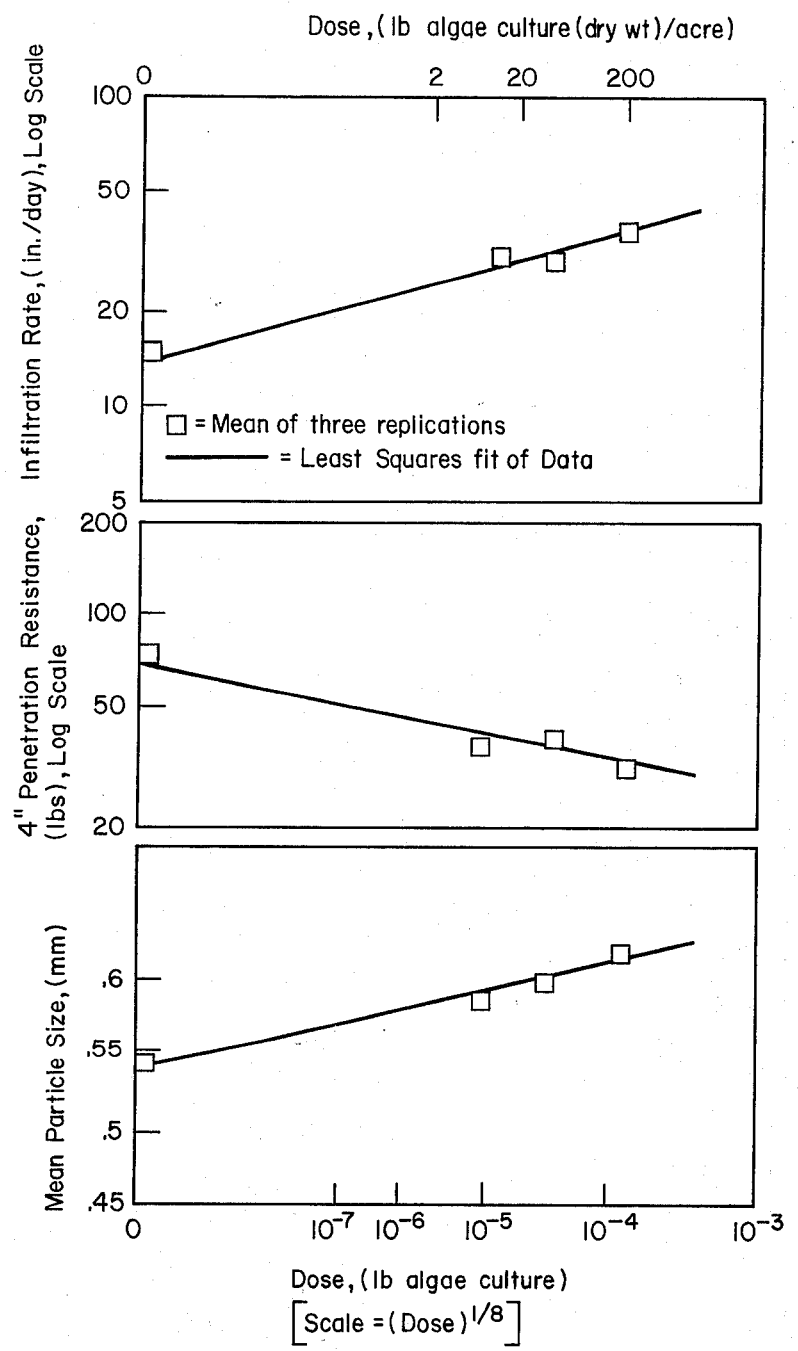
FIG. 9 illustrates the effect of applications of flocculants produced according to the invention to soil.

FIG. 9 shows a plot of each of the three physical measurements versus dose of algal flocculant applied. All values are the mean of three replications. In the horizontal scale, (dose) ⅛ was chosen so that the data fit a straight line, for illustrative purposes.

FIG. 9a shows the effect of varying levels of flocculant on water infiltration rate, measured for 8 hours at a 1-inch head. The results show a 100% increase in infiltration rate of treated plots versus untreated control plots. A dose response is also evident in the positive slope of the curve. The data is significant at the 75% level.

The effect of algal flocculant on penetration resistance is shown in FIG. 9B. This parameter is a measure of the force required to push a conical-tipped probe 4 inches into the soil. Greater than 50% decrease in resistance occurred as a result of treatment with flocculant. A dose response is indicated by the slope of the curve. The data is significant at the 90% level.

Results shown in FIG. 9c show an increase in mean particle size of flocculant treated soil samples as measured by wet sieving. A 15% increase in mean particle size occurred after treatment with 200 lb/acre. More significantly, a dose response to flocculant is evident by the positive slope of the curve. The data is significant at the 97.5% level.

Although the invention has general applicability to the production of flocculating agents from algae, it is of particular utility in the production of flocculating agents from unicellular, green and non-nitrogen fixing blue-green species which are normal inhabitants of soil and fresh water. The selection of a species suitable for the purposes of the invention is first based on an evaluation of its potential for mass culture. Growth rate should preferably be a minimum of one doubling per day. Once a selection of a promising species is made, culturing is carried out under conditions in which nitrogen is restricted so that the cell becomes nitrogen deficient, i.e. below about 5% by weight of cellular nitrogen with other nutrients being favorable for growth. During this process, the production of extracellular flocculant is monitored as described herein and the greatest flocculant producers selected.

We claim:

1. A method of producing biopolymers exhibiting flocculating activity comprising: cultivating algae in the presence of light and carbon dioxide in a nutrient medium suitable for expodential growth to a predetermined population density, thereafter restricting the available nitrogen and continuing to cultivate the algae while maintaining a supply of available phosphorus and other plant nutrients in the culture medium as required so that the nitrogen content of the cells drops to below about 5%, and after the cellular nitrogen is below 5% by weight, withdrawing active flocculating agent from the culture medium.

2. A method according to claim 1 wherein the algae are selected from the group consisting of unicellular green and non-nitrogen fixing blue-green algae.

3. A method according to claim 2 wherein the algae is of the genus Chlorella.

4. A method according to claim 3, wherein the cellular phosphorus level is maintained above about 0.5%.

5. A method according to claim 2 wherein the algae is of the genus Chlamydomonas.

6. The method according to claim 5 wherein the algae is of the species *Chlamydomonas mexicana*.

7. A method according to claim 1 wherein the exposure to light is continuous when the algae are grown in the nitrogen restricted medium.

8. A method of producing polymeric material having flocculating activity from algae, comprising the steps of culturing algae in a nutrient medium under conditions promoting optimum growth for a first period of time until a predetermined cell density is reached, thereafter culturing the algae for a second period of time, depriving the algae of available nitrogen during the second period of time to reduce the cellular nitrogen content to below about 5% by weight and maintaining light, $CO_2$ and plant nutrients other than nitrogen in quantities which are not growth limiting during the second period of time.

9. A method of producing a flocculating agent which comprises culturing algae in a tank containing an aqueous nutrient medium having sufficient available nitrogen, other nutrients, and $CO_2$ in the presence of light, so as to foster exponential growth of the algae, then when a predetermined cell density is reached, transferring a portion of the algae and nutrient medium to a second tank, adding water to the second tank, in an amount proportional to the volume of algae and nutrient medium transferred to thereby reduce the percentage content of nitrogen in the medium, supplementing the second tank with plant nutrients other than nitrogen so that growth of the algae is not limited by such other nutrients and continuing the culturing in the second tank until a predetermined cell density is reached.

10. A method according to claim 9 wherein the second tank is substantially continuously exposed to light during the culturing step.

11. A method according to claim 9 wherein the alga is selected from the genus Chlamydomonas.

12. A method according to claim 11 wherein the alga is the species *Chlamydomonas mexicana*.

13. A method of producing a flocculating agent comprising first cultivating algae in the presence of light and $CO_2$ in a nutrient medium favoring cell multiplication until a predetermined population density is reached, thereafter continuing to cultivate the algae in the presence of light and CO in a nutrient medium deficient in nitrogen but having other plant nutrients available in quantities which are not growth limiting thereby favoring the production of flocculating agent.

14. A method of producing algal biopolymers having flocculating activity comprising, culturing algae in an aqueous nutrient medium rich in available nitrogen and other required plant nutrients under conditions which favor exponential growth of the algae until the culture reaches a predetermined density, thereafter continuing to culture the algae in a nutrient medium deficient in available nitrogen but having other plant nutrients in sufficient supply so that growth is not limited by the absence of such other nutrients until nitrogen content of the algal cells drops below about 5% by weight.

* * * * *